US009713579B2

(12) United States Patent
Elia et al.

(10) Patent No.: US 9,713,579 B2
(45) Date of Patent: Jul. 25, 2017

(54) COMBINED MEASURE POSITIONING AND/OR MONITORING OF A NASO/OROGASTRIC FEEDING TUBE

(71) Applicant: ART Healthcare Ltd., Natania (IL)

(72) Inventors: Liron Elia, Kiryat-Ata (IL); Gavriel J. Iddan, Haifa (IL)

(73) Assignee: ART Healthcare Ltd., Natania (IL)

( * ) Notice: Subject to any disclaimer, the term of this patent is extended or adjusted under 35 U.S.C. 154(b) by 0 days.

(21) Appl. No.: 14/902,063

(22) PCT Filed: Mar. 12, 2015

(86) PCT No.: PCT/IL2015/050262
§ 371 (c)(1),
(2) Date: Dec. 30, 2015

(87) PCT Pub. No.: WO2015/136540
PCT Pub. Date: Sep. 17, 2015

(65) Prior Publication Data
US 2016/0151248 A1    Jun. 2, 2016

Related U.S. Application Data

(60) Provisional application No. 61/952,198, filed on Mar. 13, 2014.

(51) Int. Cl.
A61B 5/05    (2006.01)
A61J 15/00   (2006.01)
(Continued)

(52) U.S. Cl.
CPC ......... A61J 15/0088 (2015.05); A61B 5/0538 (2013.01); A61B 5/068 (2013.01);
(Continued)

(58) Field of Classification Search
CPC ... A61B 5/037; A61B 5/14539; A61B 5/4238; A61J 15/0003; A61J 15/0073
(Continued)

(56) References Cited

U.S. PATENT DOCUMENTS

2008/0097179 A1    4/2008  Russo
2008/0306411 A1   12/2008  Stuebe et al.
(Continued)

FOREIGN PATENT DOCUMENTS

WO    WO 2008/107872    9/2008
WO    WO 2015/136540    9/2015

OTHER PUBLICATIONS

International Search Report and the Written Opinion Dated Jul. 5, 2015 From the International Searching Authority Re. Application No. PCT/IL2015/050262.
(Continued)

Primary Examiner — Max Hindenburg
Assistant Examiner — Jonathan M Foreman

(57) ABSTRACT

A system for positioning of a naso/orogastric feeding tube. The system comprises an interface adapted to receive a combined impedance measure comprising a plurality of impedance readings from a plurality of impedance sensors disposed in a plurality of segments along a lateral surface of a naso/orogastric feeding tube; wherein one of the plurality of segments is located to be at least 1 centimeters above another of the plurality of segments when the naso/orogastric feeding tube is in a feeding position, a code store for storing a code, a processor coupled to the interface and the program store for implementing the stored code, the code comprising code to calculate an estimation of a position of the naso/orogastric feeding tube according to the combined
(Continued)

impedance measure, and code to generate instructions for a caregiver to relocate the naso/orogastric feeding tube according to the estimation.

16 Claims, 13 Drawing Sheets

(51) Int. Cl.
*A61B 5/053* (2006.01)
*A61B 5/06* (2006.01)
*A61B 5/00* (2006.01)

(52) U.S. Cl.
CPC .......... *A61B 5/6852* (2013.01); *A61B 5/7282* (2013.01); *A61B 5/746* (2013.01); *A61J 15/0003* (2013.01)

(58) Field of Classification Search
USPC ........................................................ 600/547
See application file for complete search history.

(56) References Cited

U.S. PATENT DOCUMENTS

| | | |
|---|---|---|
| 2010/0030133 A1 | 2/2010 | Elia et al. |
| 2010/0130854 A1 | 5/2010 | Shachar et al. |
| 2010/0274225 A1 | 10/2010 | Nishtala |
| 2012/0016256 A1* | 1/2012 | Mabary ................ A61B 5/0538 600/547 |
| 2013/0158514 A1 | 6/2013 | Elia et al. |

OTHER PUBLICATIONS

International Preliminary Report on Patentability Dated Sep. 22, 2016 From the International Bureau of WIPO Re. Application No. PCT/IL2015/050262.
Supplementary European Search Report and the European Search Opinion Dated Jul. 22, 2016 From the European Patent Office Re. Application No. 15761629.3.

* cited by examiner though the patient's pharynx and esophagus directly into the stomach, the duodenum or jejunum. One of the difficulties of naso/orogastric feeding is the increased occurrence of aspiration pneumonia caused by reflux-stomach contents going up to the pharynx of the patient initial incorrect feeding tube placement or tube migration while feeding.

COMBINED MEASURE POSITIONING AND/OR MONITORING OF A NASO/OROGASTRIC FEEDING TUBE

RELATED APPLICATIONS

This application is a National Phase of PCT Patent Application No. PCT/IL2015/050262 having International filing date of Mar. 12, 2015, which claims the benefit of priority under 35 USC §119(e) of U.S. Provisional Patent Application No. 61/952,198 filed on Mar. 13, 2014. The contents of the above applications are all incorporated by reference as if fully set forth herein in their entirety.

BACKGROUND

The present invention, in some embodiments thereof, relates to system and method of feeding and, more particularly, but not exclusively, to systems and methods of guiding a placement of a naso/orogastric feeding tube and the monitoring of naso/orogastric feeding tube feeding events.

Naso/orogastric feeding, such as esophageal, gastric, duodenal and/or enteral feeding is a form of alimentation and/or metabolic support in which nutrient formulas or medicaments are delivered directly to the gastrointestinal tract, the stomach, duodenum or the jejunum. In the majority of cases, nutrient administration is accomplished through use of a tube based device or system, delivering the nutrient through the patient's pharynx and esophagus directly into the stomach, the duodenum or jejunum. One of the difficulties of naso/orogastric feeding is the increased occurrence of aspiration pneumonia caused by reflux-stomach contents going up to the pharynx of the patient initial incorrect feeding tube placement or tube migration while feeding.

A common preventive measure against reflux of stomach contents has been to elevate the patient's upper body into a semi-recumbent position (approximately 45°), thereby reducing the ascension of gastric material up the esophagus into the pharynx and lungs.

SUMMARY

According to some embodiments of the present invention, there is provided a system for positioning of a naso/orogastric feeding tube. The system comprises an interface adapted to receive a combined impedance measure comprising a plurality impedance readings from a plurality of impedance sensors disposed in a plurality of segments along a lateral surface of a naso/orogastric feeding tube; wherein one of the plurality of segments is located to be at least 1 centimeter above another of the plurality of segments when the naso/orogastric feeding tube is in a feeding position, a code store for storing a code, a processor coupled to the interface and the program store for implementing the stored code, the code comprising: code to calculate an estimation of a position of the naso/orogastric feeding tube according to the combined impedance measure, and code to generate instructions for a caregiver to relocate the naso/orogastric feeding tube according to the estimation.

Optionally, one of the plurality of segments is located to be in the lower esophageal sphincter (LES) when the naso/orogastric feeding tube is in a feeding position in the esophagus and another of the plurality of segments is at least 1 centimeter above the LES when the naso/orogastric feeding tube is in the feeding position.

Optionally, the system comprises a man machine interface (MMI) for presenting the instructions.

Optionally, the stored code further comprises a code to detect undesired migration of the naso/orogastric feeding tube; wherein the instructions are instructions to present an alert for indicating to the caregiver to relocate the naso/orogastric feeding tube.

Optionally, the stored code further comprises a code to detect a reflux while the naso/orogastric feeding tube is in the feeding position; wherein the instructions are instructions to present an alert for indicating to the caregiver about the reflux.

Optionally, the stored code further comprises a code to detect when the naso/orogastric feeding tube is in the feeding position according to the combined impedance measure.

More optionally, the stored code further comprises a code that in response to the detection perform at least one of instructing the presentation of a user interface allowing the caregiver to initiate a feeding process using the naso/orogastric feeding tube and automatically instructing a feeding machine to initiate the feeding process.

Optionally, the system further comprises a fluid source which is mechanically connected to at least esophageal elastic body mounted on the naso/orogastric feeding tube. The stored code further comprises: a code to monitor the combined impedance measure, a code to detect an intervention event according to a change in the combined impedance measure, a code to forward inflating or deflating instructions to the fluid source in response to the intervention event detection.

Optionally, the system further comprises a display which is electronically connected to the processor. The stored code further comprises: a code to monitor the combined impedance measure, a code to detect an intervention event according to a change in the combined impedance measure, and a code to forward instructions to present an alert in response to the intervention event detection.

Optionally, the stored code further comprises: a code to detect a misplacement of at least part of the naso/orogastric feeding tube in the trachea according to the combined impedance measure, and a code to forward instructions to present an alert in response to the misplacement detection.

Optionally, the instructions comprises instructions to push the naso/orogastric feeding tube and instructions to pull the naso/orogastric feeding tube after a location of the plurality of segments in the stomach is estimated based on the combined impedance measure.

Optionally, the stored code further comprises: a code to monitor the combined impedance measure, a code to detect an intervention event according to a change in the combined impedance measure, and a code to forward instructions to regulate a feeding rate in response to the intervention event detection.

Optionally, each one of the plurality of impedance sensors is a pair of electrodes.

More optionally, each of the pair of electrodes is a portion of a wire exposed by at least one recess in a lateral surface of the naso/orogastric feeding tube.

Optionally, at least one of the plurality of segments comprises at least three electrodes which are circumferentially arranged in respective the segment around a perimeter of the naso/orogastric feeding tube; wherein each one of the plurality of impedance sensors in the respective segment comprises a pair of electrodes from at least three electrodes.

According to some embodiments of the present invention, there is provided a method for positioning of a naso/orogastric feeding tube. The method comprises inserting a naso/orogastric feeding tube having a plurality of impedance sensors disposed in a plurality of segments along a lateral surface of the naso/orogastric feeding tube into the esophagus of a patient; wherein one of the plurality of segments is located to be in the lower esophageal sphincter (LES) when the naso/orogastric feeding tube is in a feeding position in the esophagus and another of the plurality of segments is at least 1 centimeter above the LES, receiving a plurality impedance readings from the plurality of impedance sensors, calculating an estimation of a position of the naso/orogastric feeding tube according to the plurality impedance readings, and generating instructions for a caregiver to relocate the naso/orogastric feeding tube according to the estimation.

According to some embodiments of the present invention, there is provided a disposable naso/orogastric feeding tube. The disposable naso/orogastric feeding tube comprises a naso/orogastric feeding tube, and a plurality of impedance sensors disposed in a plurality of segments along a lateral surface of the naso/orogastric feeding tube. One of the plurality of segments is located to be in the lower esophageal sphincter (LES) when the naso/orogastric feeding tube is in a feeding position in the esophagus and another of the plurality of segments is at least 1 centimeter above the LES when the naso/orogastric feeding tube is in the feeding position.

Optionally, each one of the plurality of impedance sensors in a pair of electrodes.

More optionally, each of the pair of electrodes is a portion of a wire exposed via a recess in a lateral surface of the naso/orogastric feeding tube.

Optionally, at least one of the plurality of segments comprises at least three electrodes which are circumferentially arranged in respective the segment around a perimeter of the naso/orogastric feeding tube; wherein each one of the plurality of impedance sensors in the respective segment comprises a pair of electrodes from at least three electrodes.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5A) and/or monitoring process (e.g. FIG. 5B), according to some embodiments of the present invention;

DETAILED DESCRIPTION

Figure 1:
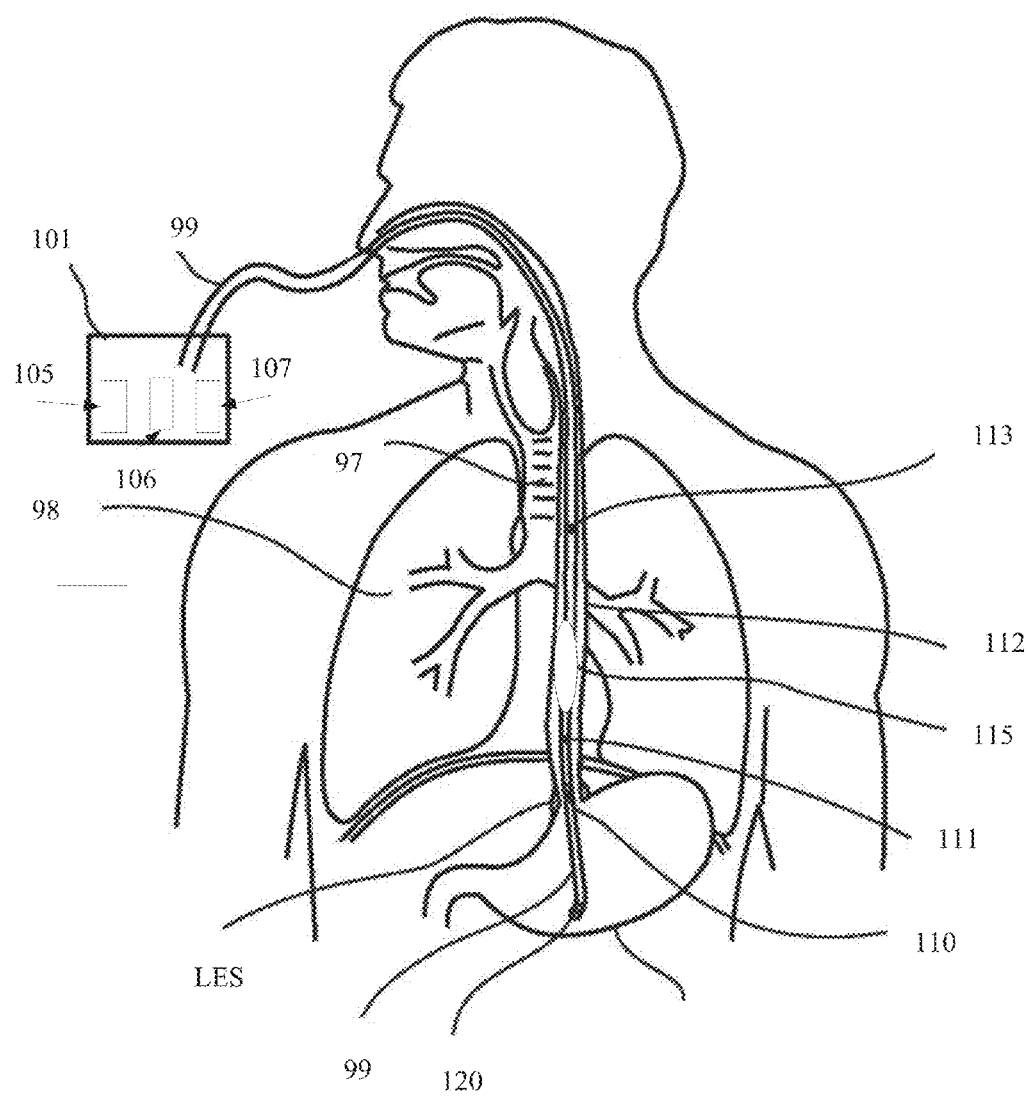
FIG. 1 is a schematic illustration of a portion of a naso/orogastric feeding tube having a plurality of impedance sensors for detecting positioning of the naso/orogastric feeding tube in the esophagus and/or a reflux in the esophagus and a control device which is electronically connected to the impedance sensors, according to some embodiments of the present invention.

The present invention, in some embodiments thereof, relates to system and method of feeding and, more particularly, but not exclusively, to systems and methods of guiding a placement of a naso/orogastric feeding tube and the monitoring of naso/orogastric feeding tube feeding events.

According to some embodiments of the present inventions, there are provided methods and systems of positioning a naso/orogastric feeding tube based on a real time analysis of readings of sensors, such as impedance sensors which are disposed to sense a feedback from the digestive system in at least two to segments along the surface of the naso/orogastric feeding tube. For example, a combined impedance measure that includes impedance readings from different segments along the surface of the naso/orogastric feeding tube is analyzed to determine whether the lower segment is in the lower esophageal sphincter (LES), in the esophagus and/or in the stomach. Optionally, the distance between segments (e.g. between the boundaries of each segment, for instance boundaries determined by the sensing areas of the sensors) is at least 1 centimeter (cm), for instance 1-5 cm or 4-5 cm any intermediate value.

Optionally, each sensor is a pair of electrodes. The electrodes are optionally portions of wires threaded along the naso/orogastric feeding tube and exposed to the area around the naso/orogastric feeding tube via recesses. Optionally, the electrodes are circumferentially arranges around the perimeter of the segment of the naso/orogastric feeding tube (e.g.

an annular segment). This allows detecting a misplacement of the naso/orogastric feeding tube in the trachea. Optionally, the system includes presentation means such as a display to present instructions and/or alerts during the positioning process and based on a combined measure that combines readings of the sensors from different segments, for instance combined impedance measure. The display may instruct the user to push or pull naso/orogastric feeding tube toward or from a feeding position. In use, after the naso/orogastric feeding tube is placed in the feeding position, feeding may be initiated and a monitoring process that is based on the readings of the sensors can be triggered.

According to some embodiments of the present inventions, there are provided methods and systems of monitoring a naso/orogastric feeding tube based on a real time analysis of readings of sensors, such as impedance sensors which are disposed to sense a feedback from the digestive system in at least two segments along the surface of the naso/orogastric feeding tube. For example, a combined impedance measure that includes impedance readings from different segments along the surface of the naso/orogastric feeding tube is analyzed to determine whether the lower segment or any other portion of the naso/orogastric feeding tube moved after being positioned in a feeding position. Optionally, the distance between segments (e.g. between the boundaries of each segment, for instance boundaries determined by the sensing areas of the sensors) is at least 1 centimeter (cm), for instance 1-3 or 3-4 cm or any intermediate value. Optionally, a real time analysis of the combined impedance measure is conducted to identify reflux. When an intervention event, such as an desired movement of the naso/orogastric feeding tube or reflux is detected, automatic measure may be instructed by a control unit implementing the monitoring, for instance instructing the presentation of an alert, instructing the changing the pressure in an elastic body used for blocking reflux, and/or instructing the operation of valves and/or a feeding machine to control a feeding flow rate.

According to some embodiments of the present inventions, there is provided a naso/orogastric feeding tube having impedance sensors electrically connected to a control unit to determine, based on a combined measure that combines impedance readings from the impedance sensors, a current position, a reposition and/or a presence or an absence of reflux. Such a determination allows the control unit to instruct and/or an alert a caregiver in real time, preventing or reducing the risk of naso/orogastric feeding phylogenies, such as tube misplacement, overfeeding, tube movement and/or the like.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or block.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference is now made to FIG. 1, which is a schematic illustration of a system 100 having a control unit 101 that is electrically connected to impedance sensors in a plurality of segments, for example see some or all of 110-113, mounted on a naso/orogastric feeding tube 99 and adapted to guide a caregiver during a positioning process and/or to manage intervention events during a monitoring procedure, according to some embodiments of the present invention. The naso/orogastric feeding tube 99 is located in a feeding position in the esophagus. The control unit 101 guides and/or monitor according to a combined impedance measure that combines reading from the impedance sensors. The control unit may be a console having one or more mechanical values to control a feeding rate via a feeding tube connected between the naso/orogastric feeding tube 99 and a feeding machine. While positioning, the combined impedance measure allows the control unit 101 to instruct a caregiver how to manipulate the naso/orogastric feeding tube 99 to a feeding position in the esophagus. While monitoring, the combined impedance measure allows the control unit 101 to automatically detect positioning and/or a movement of the naso/orogastric feeding tube 99 in the esophagus and/or a reflux in the esophagus. The control unit 101 may include or be connected to a man machine interface (MMI) 105, such as a screen, for example a touch screen and includes a code storage 106 for storing a code for implementing the processes described below by a processor 107. The control unit 101 is optionally electrically connected to some or all of the impedance sensors 110-113 in a disposable naso/orogastric feeding tube 99 via a communication interface, such as a plug. The control unit 101 may be implemented as a measuring circuit having at least a processor, memory and one or more microcontrollers. The impedance sensors 110-113 may be embedded into the disposable naso/orogastric feeding tube 99 or provided in a sheath fitted to a feeding tube. When the impedance sensors 110-113 are in a sheath, a regular feeding tube can be used.

The control unit 101 and/or the system and/or the impedance sensors are optionally as defined in international Patent Publication Number WO2011092701 which is incorporated herein by reference. The naso/orogastric feeding tube 99 having an inner lumen (not shown) for delivering nutrients, microorganisms, water and/or medications. The naso/orogastric feeding tube 99 is sized and shaped as any commonly used naso/orogastric feeding tube, for example a naso/orogastric feeding tube, a naso-esophageal catheter, a gastric feeding tube, such as a nasogastric feeding tube, a duodenal feeding tube and an enteral feeding tube. The naso/orogastric feeding tube 99 is sized and shaped for being disposed within the esophagus so that a distal end thereof is placed in the stomach lumen of a patient. Optionally, the naso/orogastric feeding tube 99 comprises a small diameter flexible tube preferably made of transparent plastic, such as polyvinyl Chloride or silicone. The length of the naso/orogastric feeding tube 99 is adjusted or selected according to the size of a target patient. For example, a naso/orogastric feeding tube is of more than 120 centimeter long for 14 Fr tube for adults and a naso/orogastric feeding tube for infants is of more than 40 centimeter long for 5 Fr tube.

As outlined above, the naso/orogastric feeding tube 99 further comprises one or more impedance sensors (at least in segments 111-112) for detecting impedance in a number of segments along the naso/orogastric feeding tube 99 and the esophagus. For example, while one or more impedance sensors are disposed (or mounted interchangeably) to be located in the lower esophageal sphincter (LES) when the naso/orogastric feeding tube 99 is in a feeding position the one or more other impedance sensors are mounted to be located at least 2 centimeters above the LES when the naso/orogastric feeding tube 99 is in the feeding position. In use, when placed in the esophagus, the control unit 101 generates a combined impedance measure for detecting positioning and/or a movement of the naso/orogastric feeding tube in the esophagus and/or a reflux in the esophagus based on the reading of the impedance sensors (at least in segments 111-112), for example as described below.

Optionally, one or more esophageal elastic bodies having an adjustable volume, for instance a pressure dependent volume, such as balloons, are positioned along the naso/orogastric feeding tube 99 and mechanically connected to be inflated or deflated by a fluid source, such as a pump assembly or a pressure tank controlled by the control unit 101. For brevity, the one or more esophageal elastic bodies are referred to herein as elastic esophageal body 115. The elastic esophageal body 115 may be connected to a distal end of one or more air conducting tube(s) for inflating and/or deflating the elastic esophageal body 115. The proximal end of the air conducting tube is optionally connected to the fluid source that inflates the elastic esophageal body 115 based on instructions from the control unit 101. Optionally, the elastic esophageal body 115, which is connected to the conducting tube, is connected to pressure tank that releases or increases the pressure in high speed to deflate or inflate the elastic body in high speed, for example as further described below. Optionally, the fluid source is a bidirectional pump assembly that allows inflating and deflating the elastic esophageal body 115 optionally when using pressure tank, the deflating or inflating of the elastic body is controlled by adapting fluid rate from the pressure tank.

Optionally, each impedance sensor includes a pair of electrodes along a line traversing the longitudinal axis of the naso/orogastric feeding tube 99 or located in parallel to the longitudinal axis of the naso/orogastric feeding tube 99.

Figure 2:
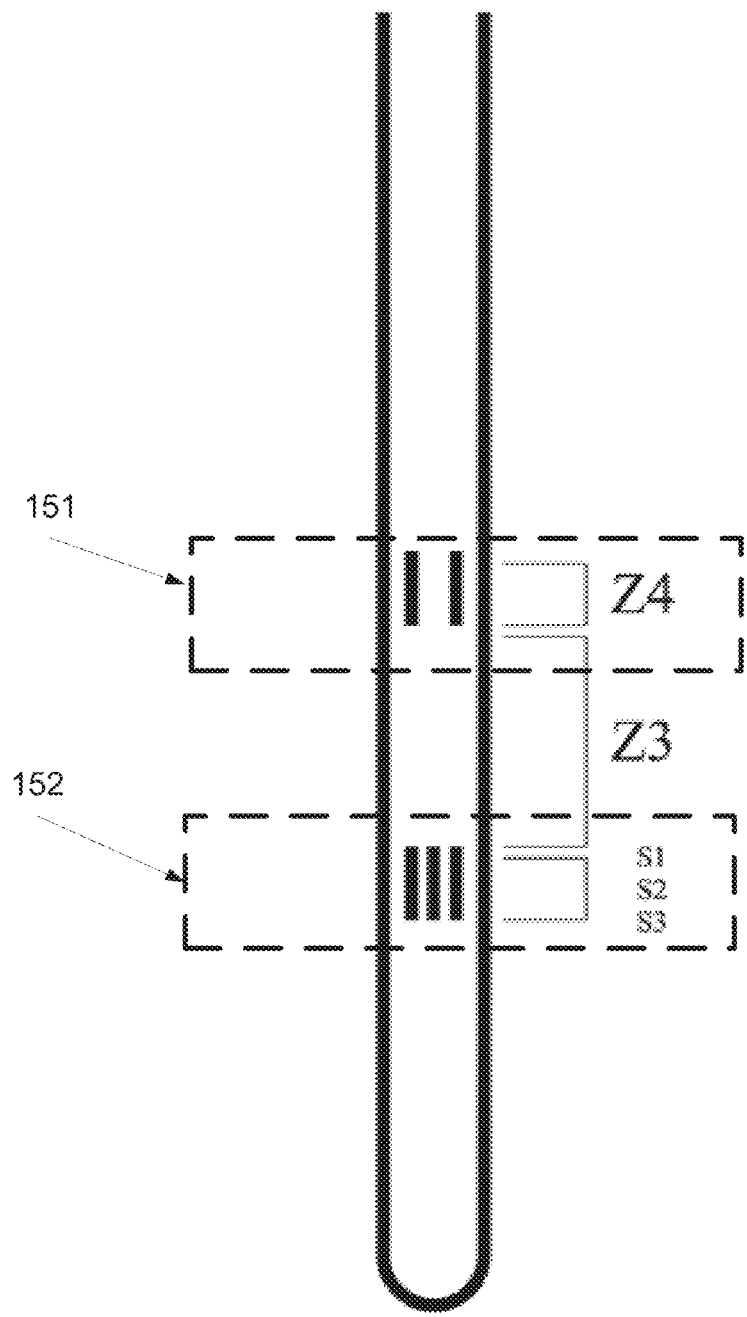
FIG. 2 is an exemplary tip of a naso/orogastric feeding tube and the location of electrodes functioning as exemplary impedance sensors thereon, according to some embodiments of the present invention.

Pair(s) of electrodes are located at different segments where one segment is located above another segment, for instance such that at least 2 centimeters (cm) separate electrodes on one segment from electrodes on another segment, for example 3 cm, 4 cm or any intermediate or longer distance apart, see for example FIG. 2 that depicts segment 151 and segment 152 in dashed line squares. The lower segment 152 is located to be placed in the LES when the naso/orogastric feeding tube 99 conducts feeding content and may be referred to herein as a LES segment. The upper segment 151 is located to be placed above the LES when the naso/orogastric feeding tube 99 conducts feeding content and may be referred to herein as an esophagus segment 151.

Figure 3A:
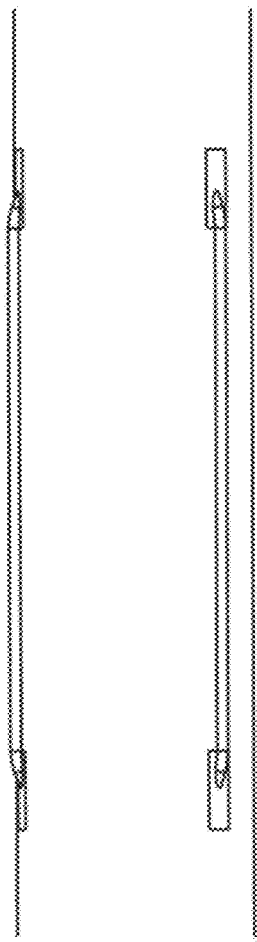
FIGS. 3A-3C are exemplary electrodes functioning as exemplary impedance sensors, according to some embodiments of the present invention.
Figure 3B:
Figure 3C:
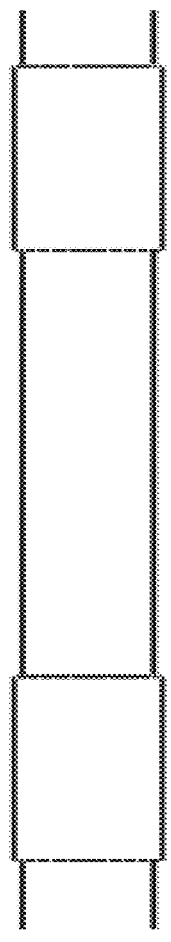

Optionally, each impedance sensor 102 includes one or more annular or helical electrodes, for example as shown at FIG. 3C. Optionally, each impedance sensor 102 includes two or more strip electrodes, optionally parallel, which are circularly and dividedly placed around a common segment of the naso/orogastric feeding tube 101.

Optionally, the electrodes are segments of wires threaded along the naso/orogastric feeding tube 101, for instance as depicted in FIGS. 3A and 3B or conductive elements connected to the threaded wires. In such embodiments, wires are threaded in the naso/orogastric feeding tube 99, for example in channels which are formed therein; see also FIGS. 8 and 9A and 9B of international Patent Publication Number WO2011092701 that is incorporated herein by reference. In order to allow the sensors formed along the wires to detect changes in the impedance around the naso/orogastric feeding tube 99, for example in the esophageal lumen, openings, such as cuts, optionally longitudinal, are formed in one or more locations along the channels, optionally in different heights with reference to the tip 120 of the naso/orogastric feeding tube 99, see for example FIGS. 3A-3B. In use, the wires which are treaded above the surface of the naso/orogastric feeding tube 99 (e.g. FIG. 3A) allow a direct contact with the walls of the esophageal lumen. The wires which are located in recesses formed in the surface of the naso/orogastric feeding tube 99 (e.g. FIG. 3B) allow detection of a presence of GI fluids therearound. Both types of sensors detect impedance changes in different segments of the naso/orogastric feeding tube 101.

Optionally, each electrode covers an area of about 1 mm$^2$ and 150 mm$^2$. Optionally, between 2 and 20 electrodes are used in each impedance sensor 110-113. Optionally, the distance between each pair of parallel electrodes is between about 3 mm and about 30 mm.

Optionally, the electrode is made of steel, stainless steel, brass, copper, platinum, silver, gold, aluminum alloy, zinc, nickel, tin, magnesium alloy, bronze, phosphor bronze, conductive polymers and/or any composition thereof and/or any medical grade alloy therefrom.

Optionally, the electrodes are printed on the peripheral surface of the naso/orogastric feeding tube 101. Optionally, the electrodes are coated with Gold, Silver, Nickel, Zinc, Tin, Copper and/or any composition thereof and/or any alloy therefrom.

Optionally, the electrodes are shaped as Circular, rectangular, and/or triangular spots.

Optionally, three electrodes or more are circumferentially arranged in the LES segment 152, for instance such that about a third of the perimeter of the naso/orogastric feeding tube 99 separates between one electrode and another. Each of these electrodes is optionally a portion of a wire threaded along the naso/orogastric feeding tube 99 as depicted in FIG. 3A. In an exemplary arrangement electrodes X1-X3 are located in LES segment 152 to form 3 impedance sensors S1-S3, each from a pair selected from electrodes X1-X3 (S1-X1-X2 and S2-X2-X3 and S3-X3-X1) and electrodes Y3-Y4 are located in esophagus segment 151 to form 2 impedance sensors Z3-Z4 (Z3-Y3-Y4 and Z4-Y4-Y3). The LES segment 152 is sized and shaped to be in the LES when the esophagus segment is at least 2 cm above the LES.

An arrangement of three or more electrodes along the perimeter of a segment of the naso/orogastric feeding tube 99 (e.g. the LES segment 152) allows detecting when the segment is in the esophagus, for example in the LES, and when the segment is in the trachea 97 for instance vertically to the lungs 98. Such detection is possible as the lumen of the esophagus and the LES contracts around the naso/orogastric feeding tube 99 and the lumen of the trachea remains in a fixed perimeter. Reading impedance values from the circumferential arraignment of impedance sensors allows calculating a combined impedance measure indicative of a placement of the LES segment 152 in the trachea or a placement of the LES segment 152 in the esophagus. This is based on analysis of the combined impedance measure and a detection of an impedance difference therein which is indicative of contact of some or all of the electrodes with the lumen walls.

For example, when the impedance sensors are pairs of electrodes, false insertion of the tip of the naso/orogastric feeding tube 99 into the trachea may be detected when the impedance difference between the impedance readings of different pairs of electrodes (each pair is an impedance sensor) is greater than a threshold. Such a difference is indicative of partial contact with the walls of the surrounding lumen. This partial contact indicates that the tip of the naso/orogastric feeding tube 99 is positioned at the trachea where the walls do not contract in response to the insertion of an object or esophageal peristalsis. In such embodiments, when the distance of each one of the electrodes from the walls of the surrounding lumen is not similar, the control unit 101 triggers an alert and/or the presentation of operator instructions. As used herein, an alert and/or a presentation are may be any audio or visual signals which are played to a caregiver (a term used herein to describe any user who operates the control unit 101).

As outlined above, readings of the impedance sensors along a surface of the naso/orogastric feeding tube 99, at the LES segment 152 and the esophagus segment 151, form the combined impedance measure. This combined impedance measure is indicative of different positions of the naso/orogastric feeding tube 99 in the intrabody lumens of a patient, for example during a process of positioning of the naso/orogastric feeding tube 99 in the esophagus for feeding.

Figure 4:
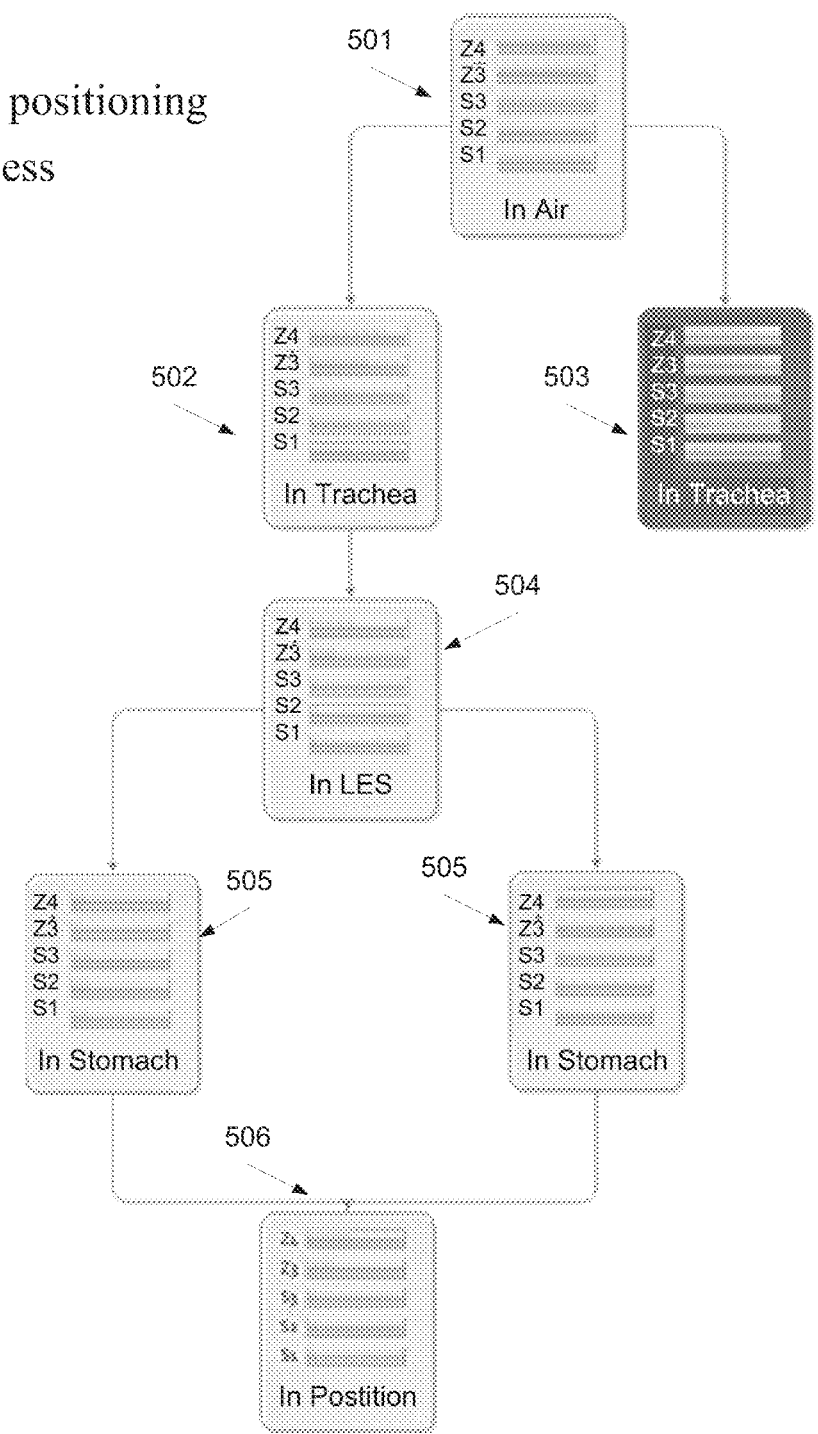
FIG. 4 is a flowchart depicting readings of combined impedance measures by electrodes threaded along naso/orogastric feeding tube during a process of detecting a positioning of naso/orogastric feeding tube in the esophagus, according to some embodiments of the present invention.

For example, FIG. 4 is a flowchart depicting a flow of different combined impedance measures taken at different events during a process of positioning of the naso/orogastric feeding tube 99 in the esophagus for feeding, according to some embodiments of the present invention. As indicated in 501, high impedance in each impedance sensor, for instance about 20,000 ohm, is measured when the LES segment 152 and the esophagus segment 151 are located outside of the body. As indicated in 502, when the naso/orogastric feeding tube 99 is in the esophagus, the readings from all the impedance sensors are similar (e.g. less than 2000 ohm difference); however, as shown at 503, when the naso/orogastric feeding tube 99 is in the trachea, the impedance difference the impedance readings of different impedance sensors (e.g. pairs of electrodes) is much greater. For clarity, an impedance difference means a difference between any pair of impedance sensors in a segment. As shown at 504 and 506, the combined impedance measure indicates when the LES segment 152 is in the LES, namely that the naso/orogastric feeding tube 99 is in a position for feeding. Such a combined impedance measure shows that an impedance difference between the reading of the impedance sensors of the LES segment 152 (around 500 ohm) and the reading of the impedance sensors of the esophagus segment 151 is greater than a threshold, for example more than 500 ohm, 1000 ohm, or around 2000 ohm or any impedance value.

As shown at 505, the combined impedance measure indicates when both the LES segment 152 and the esophagus segment 151 are in the stomach. Such a combined impedance measure shows that the readings of all the impedance sensors are lower than a threshold.

Figure 5A:
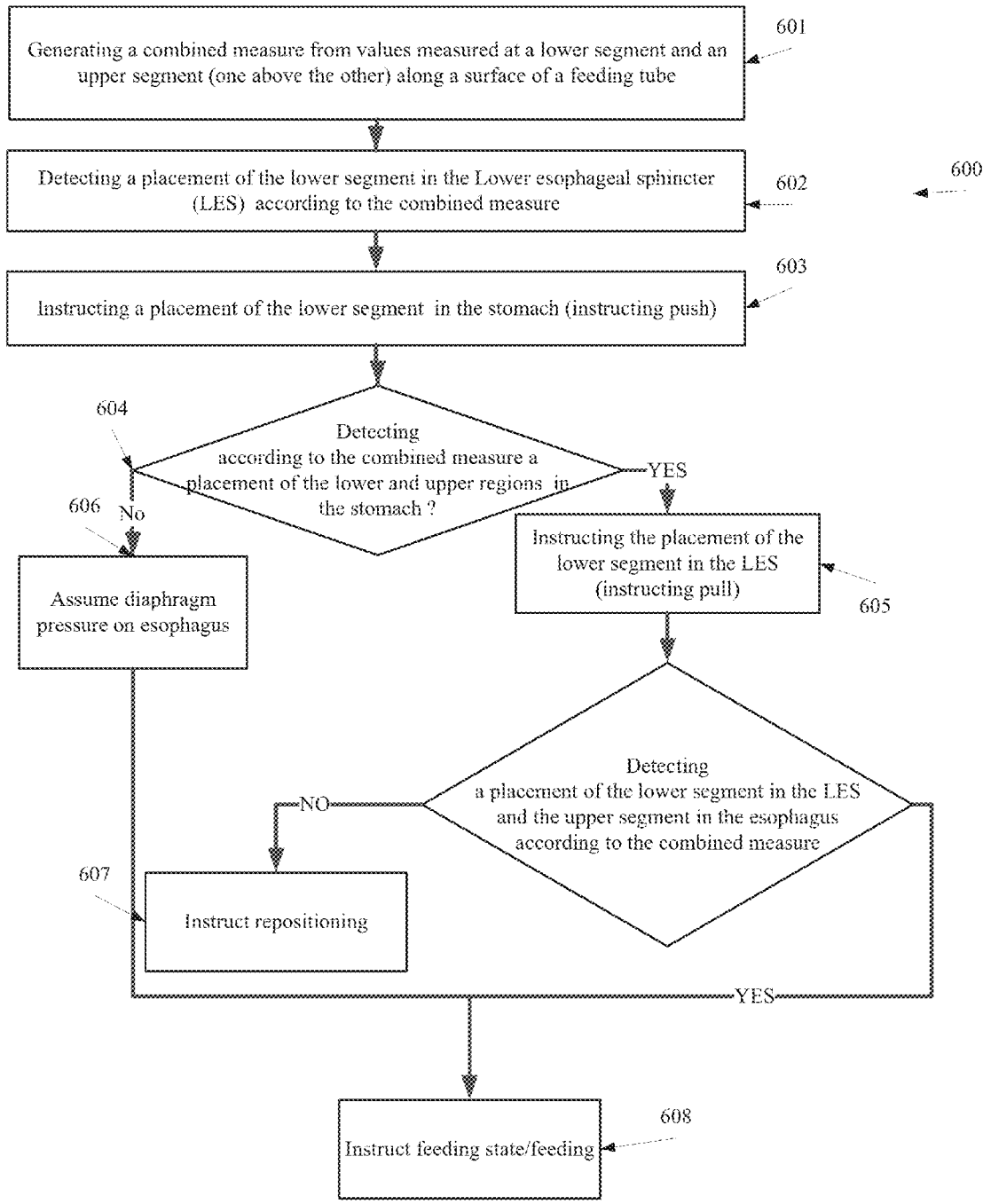
FIG. 5A is a flowchart of a process of detecting a positioning of naso/orogastric feeding tube in the esophagus based on a combined impedance measure measured by sensors in two segments on the naso/orogastric feeding tube, according to some embodiments of the present invention.

Reference is now also made to FIG. 5A, which is a flowchart of a positioning process 600 of detecting a positioning of the naso/orogastric feeding tube 99 in the esophagus based on a combined impedance measure, according to some embodiments of the present invention. The positioning process may be implemented by the processor 107 of the control unit 101 when it implements a positioning code stored in code storage.

First, as shown at 601, a combined impedance measure is an array of readings of impedance sensors in segments 151, 152, for example as described, for instance as exemplified in 501.

Now, as shown at 602, a detection of the placement of the LES segment 152 in the LES is identified by an analysis of the combined impedance measure. For example, as exemplified in 504. Optionally, this identification is determined after a positioning of the LES segment 152 in the esophagus is detected, for instance as depicted in 502.

Now, as shown at 603, and in order to avoid a false estimation of the positioning of the LES segment 152 in the LES due to diaphragm pressure caused for example by Hiatal Hernia, the caregiver is instructed to further push the naso/orogastric feeding tube 99 along the esophagus. As shown at 604, when the impedance readings of the LES segment sensors and the esophagus segment sensors is below a threshold, as shown at 505, it is assumed that both the LES segment 152 and the esophagus segment 151 are in the stomach and the caregiver is instructed to pull the naso/orogastric feeding tube 99 and to bring the lower segment sensors to be in the lumen of the LES, as shown at 605. As shown at 606, when the impedance difference between the reading of the LES segment sensors and the esophagus segment sensors is above a threshold, as shown at 506, it is assumed that the LES segment 152 is now in the LES and that the patient has diaphragm pressure caused for example by Hiatal Hernia. As shown at 607, when the combined impedance measure is not expected, repositioning is instructed, for example advancing 5 cm by pulling.

As shown at 608, now feeding may be initiated by the control unit 101 after it is assumed that the LES segment 152 is in the LES and the distal end of the naso/orogastric feeding tube 99 is in the stomach.

According to some embodiments of the present invention, the positioning process depicted in FIG. 5A is held while one or more instructions are presented to the caregiver (e.g. a physician or a nurse) so as to safely guide the positioning process.

FIGS. 6A-6E are exemplary screenshots of a graphical user interface (GUI) presented to the caregiver in a display connected to the control unit 101, according to some embodiments of the present invention. The displays are optionally generated and/or selected based on the combined impedance measure. The GUI optionally includes a presentation of the impedance reading of each impedance sensor (e.g. S1-S3 and Z3-Z4) 701 and/or emulation 702 of the current positioning of the at least part of the naso/orogastric feeding tube 99 is generated based on the combined impedance measure.

Figure 6A:
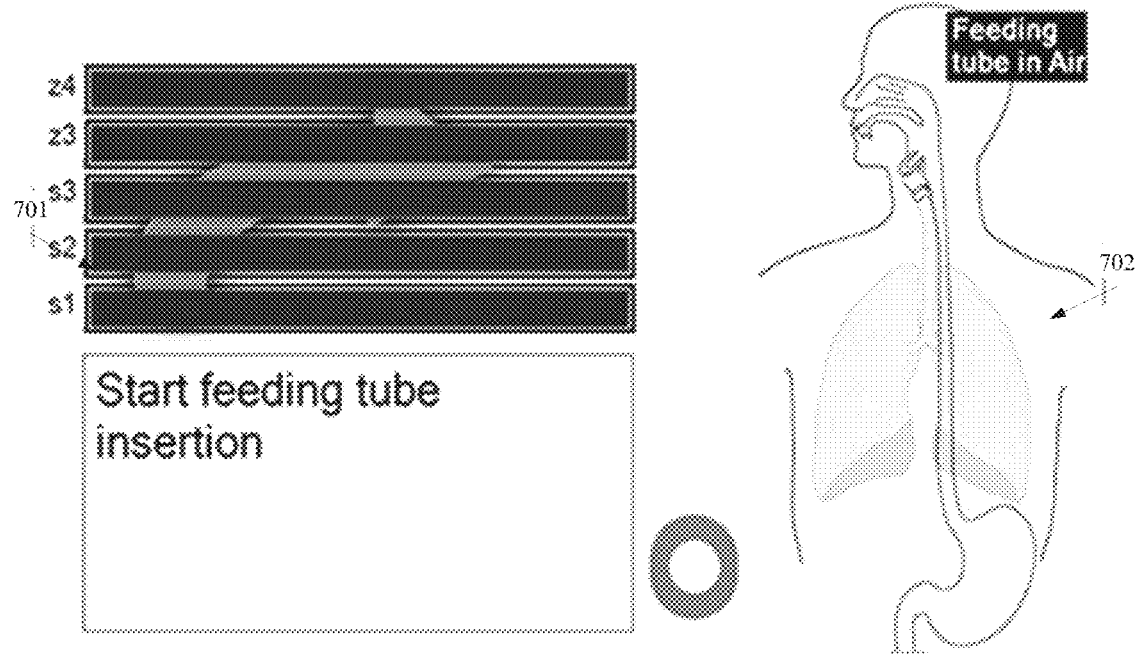
FIGS. 6A-6I are exemplary screenshots of caretaker instructions and alerts which are presented during a positioning process (e.g.
Figure 6B:
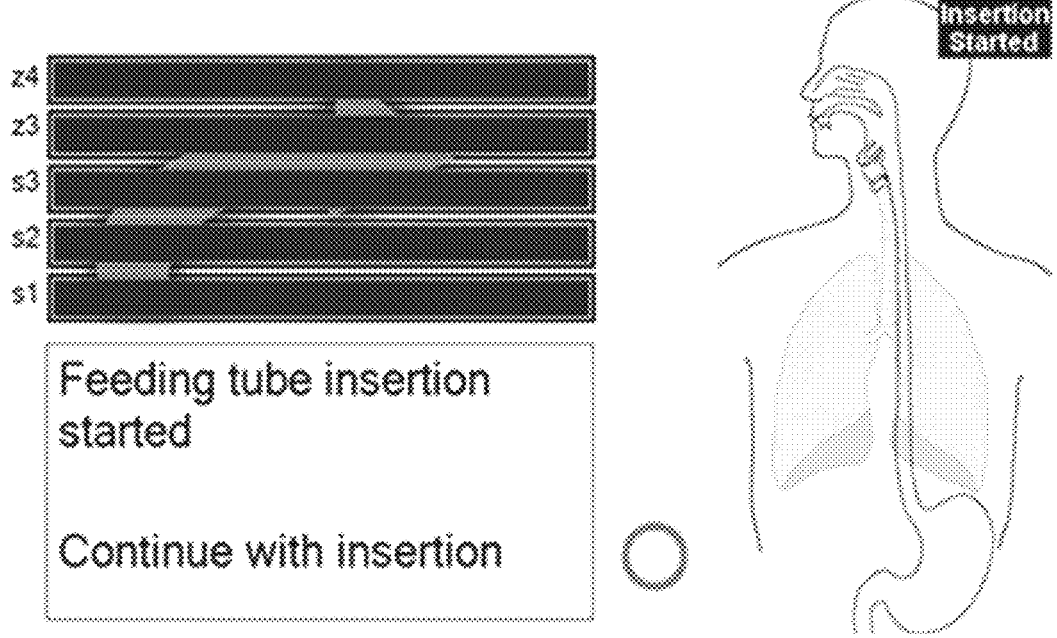
Figure 6C:
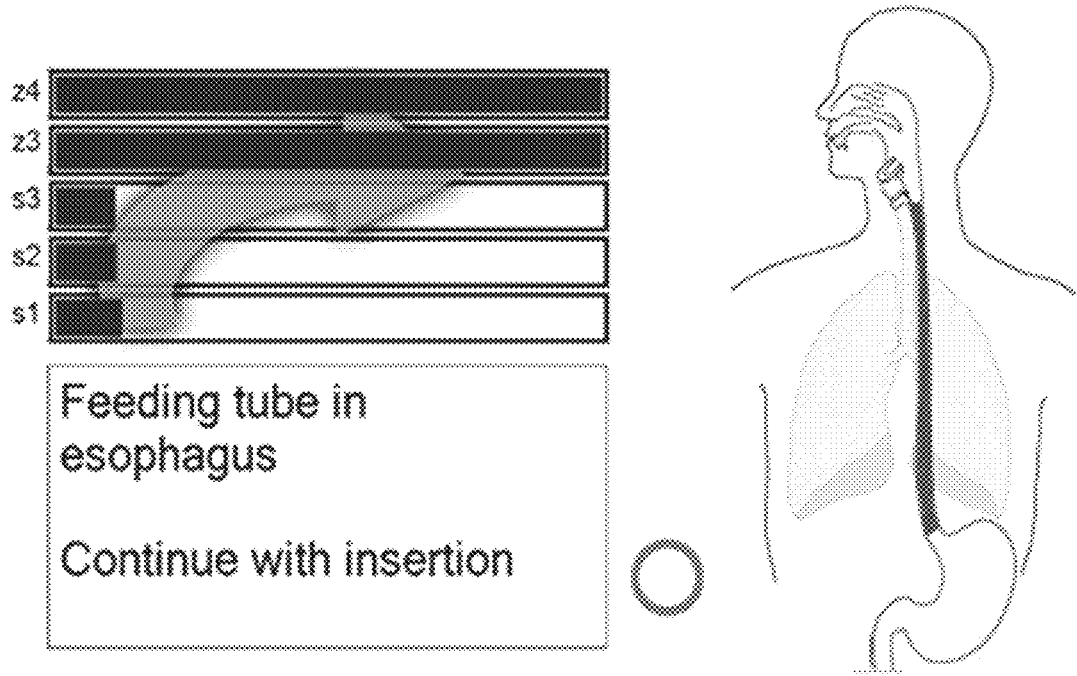
Figure 6D:
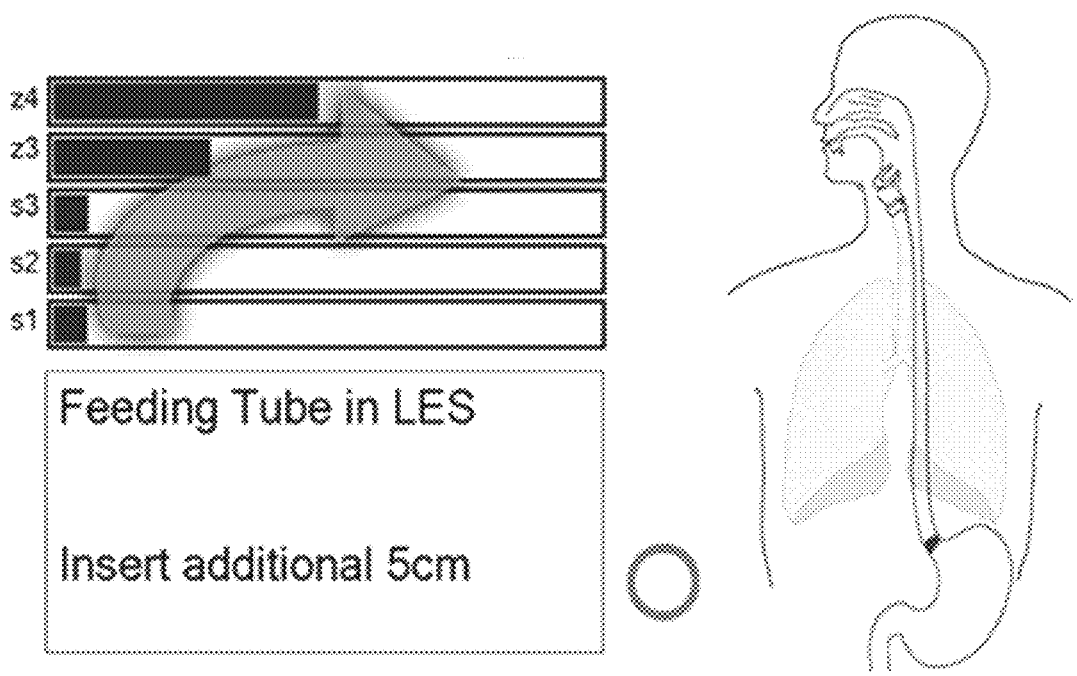
Figure 6E:
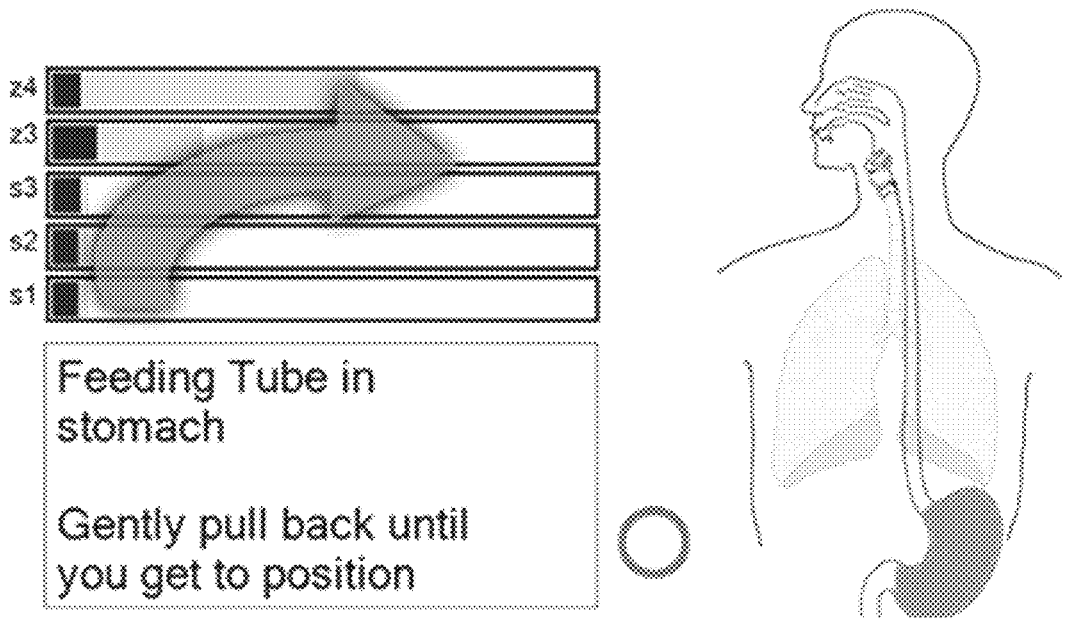

FIG. 6A, optionally correlated with the combined impedance measure measured in 601, depicts an initial state where the impedance sensors at the segments 151, 152 are exposed to air. FIG. 6B depicts a positioning start state where the impedance sensors at the segments 151, 152 are still exposed to air however the caregiver indicated to the control unit 101 that he initiates the positioning process, for example by using the MMI 105. FIG. 6C, optionally correlated with the combined impedance measure measured in 602, depicts a presentation of an indication of a detection of a state wherein segments 151 and 152 of the naso/orogastric feeding tube 99 are assumed to be in the esophagus. As indicated above with reference to 603, the caregiver is now instructed to further push the naso/orogastric feeding tube 99 into the stomach. FIG. 6D depicts a presentation of an indication of a detection of a state wherein segment 151 of the naso/orogastric feeding tube 99 is assumed to be the LES and segment 152 of the naso/orogastric feeding tube 99 is assumed to be in the esophagus. As indicated above with reference to 605 and depicted in FIG. 6E, the caregiver is now instructed to pull the naso/orogastric feeding tube 99 such that the LES segment 152 is back in the LES.

Figure 6F:
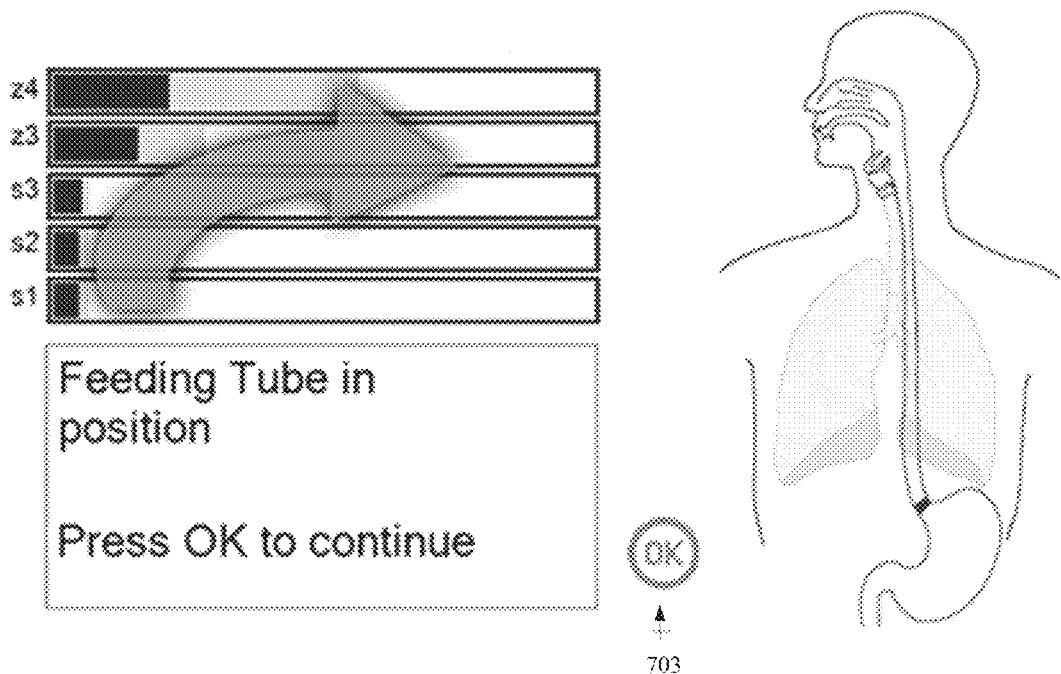

As indicated above with reference to 608 and depicted in FIG. 6F, the naso/orogastric feeding tube 99 is assumed to be in a feeding position when the LES segment 152 is back in the LES and feeding may be initiated, either automatically and/or after receiving a user confirmation, for instance manually by pressing on a designated button 703 (a fixed button or a button presented on a touch screen).

Figure 6G:
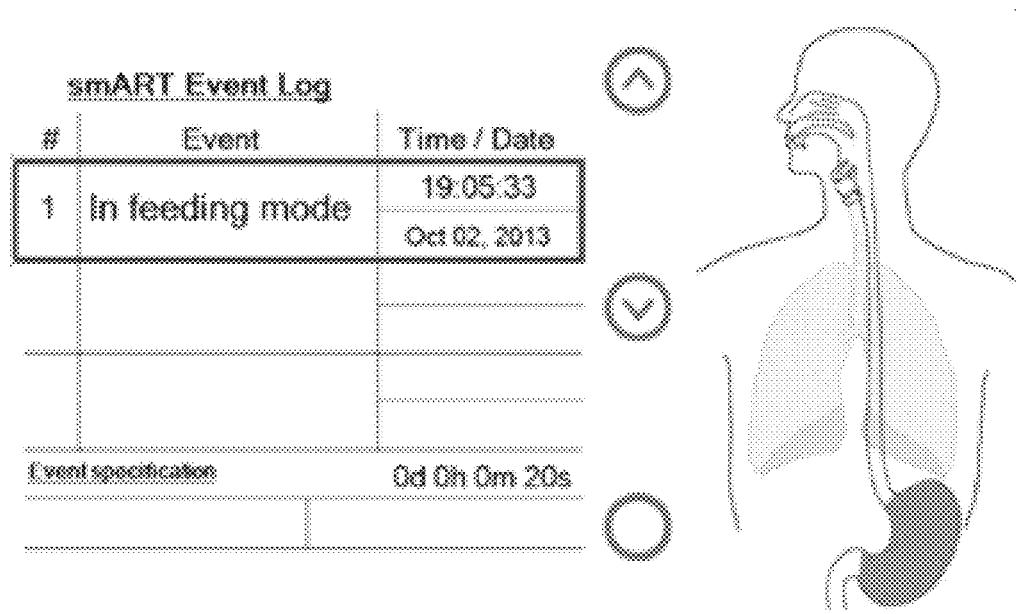

Optionally, information about the feeding process, for instance the initiation time and/or events detected during the feeding process, for instance the intervention events described below are logged. This information may be presented using the display, for instance as shown at FIG. 6G.

After the feeding starts, the combined impedance measure may be used for detecting intervention events, for instance a reflux and/or a migration of the naso/orogastric feeding tube 99, for instance unintentional migration of the tube.

Figure 5B:
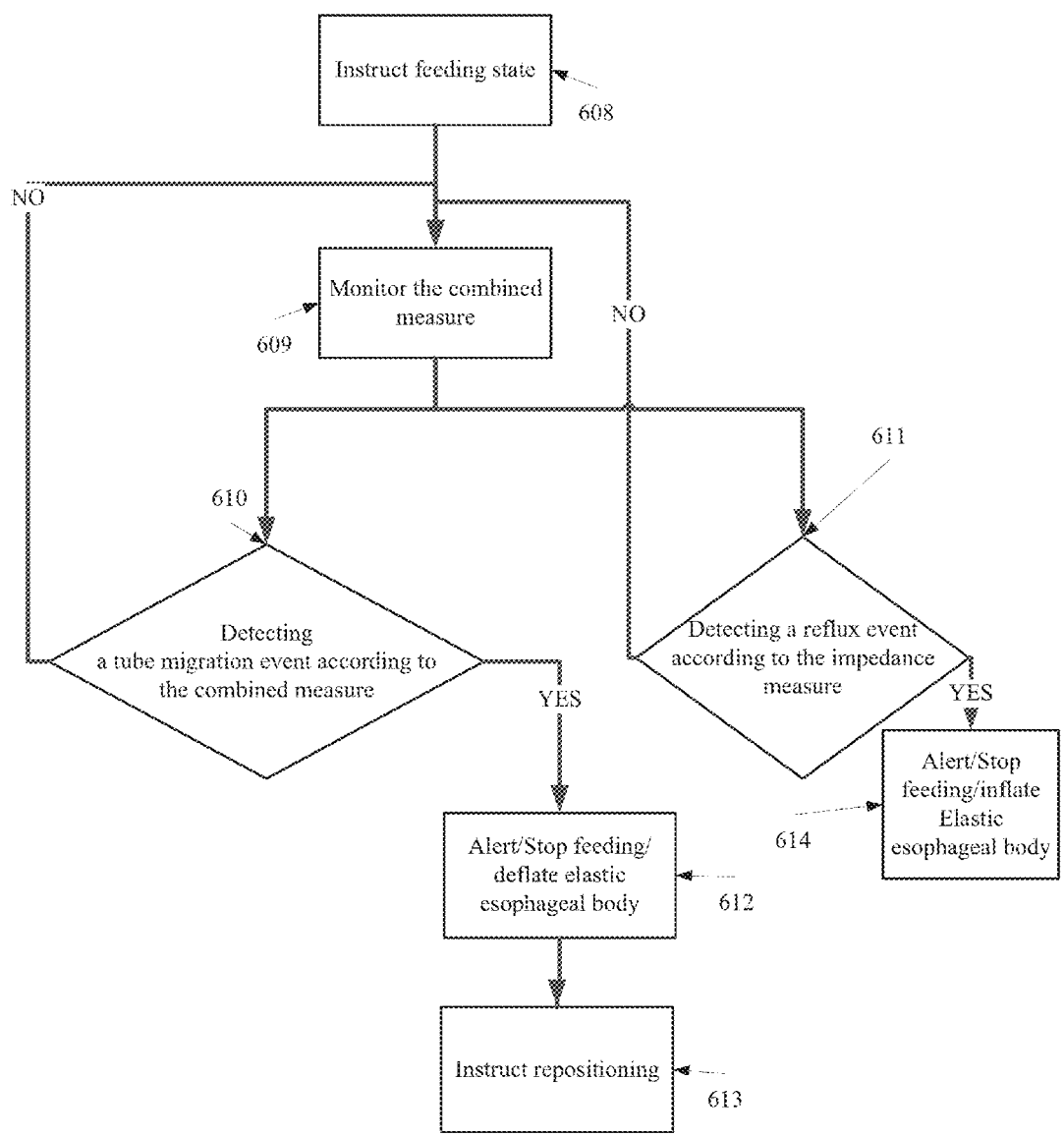
FIG. 5B is a flowchart of a process of detecting intervention events during a feeding period based on a combined impedance measure, for example a combined impedance measure as measured in FIG. 5A, according to some embodiments of the present invention.

Reference is now also made to FIG. 5B that depicts a monitoring process wherein a presence or an absence of intervention events, such as a reflux event or a tube migration event are monitored. 608 is as described above. During the feeding period, as shown at 609, changes in the combined impedance measure are measured to detect intervention events after 608. The monitoring process may be implemented by the processor 107 of the control unit 101 when it implements a monitoring code stored in code storage.

Figure 6H:
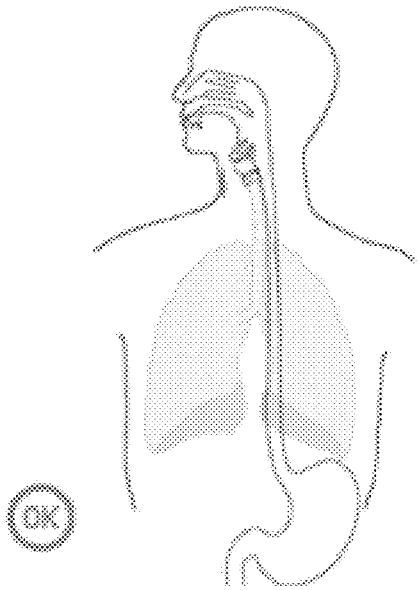

As shown at 610, when a tube migration event is detected the control unit 101 intervenes in the feeding process, for instance as shown at 612 by:

instructing the stopping the feeding, for instance by controlling a feeding machine and/or one or more mechanical values which change the flow of feeding content into the naso/orogastric feeding tube 99;

instructing the deflating the elastic esophageal body 115 by controlling the fluid source and/or one or more mechanical values which change the flow of fluid into the elastic esophageal body 115; and/or instructing a presentation of an alert, for instance by playing a sound and/or presenting a notification as depicted in FIG. 6H. The deflating is important to avoid harming the tissues surrounding the esophagus when the naso/orogastric feeding tube 99 is pulled. The tube migration event may be detected when the impedance difference between readings in segments 151 and 152 descends below a threshold, for example as region 151 and region 152 are both in the esophagus (e.g. as shown at 502) or in the stomach (e.g. as shown at 505). Optionally, as shown at 613, repositioning is instructed, for instance as described with reference to FIG. 5A.

Figure 6I:
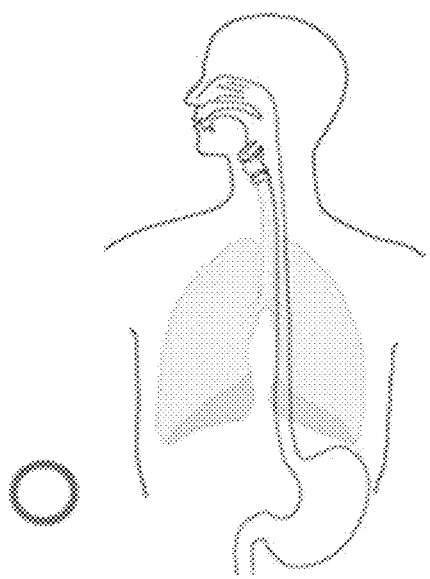

As shown at 611, when a reflux event is detected the control unit 101 intervenes in the feeding process, for instance as shown at 614 by:

instructing the stopping the feeding, for example by instructing a feeding machine or controlling valves as described above;

instructing the inflating of the elastic esophageal body 115, for example by instructing the fluid source or controlling valves as described above; and/or instructing a presentation of an alert, for instance by playing a sound and/or presenting a notification as depicted in FIG. 6I. The inflating is important to prevent from the reflux from getting to the trachea and to reduce the risk of feeding content aspiration. The reflux event may be detected when the impedance difference between readings in segments 151 and 152 descends below a threshold. Optionally, as shown at 613, repositioning is instructed, for instance as described with reference to FIG. 5A.

Figure 7A:
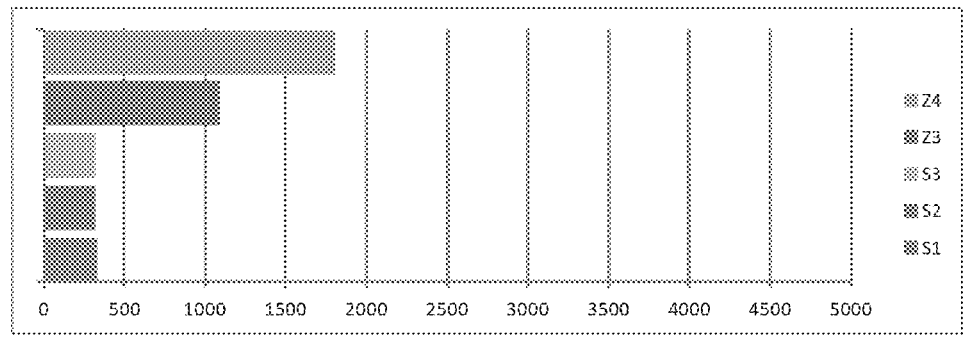
FIGS. 7A-7D are exemplary combined impedance measures measured at different events held while positioning a naso/orogastric feeding tube of a naso/orogastric feeding device and monitoring impedance near the naso/orogastric feeding tube in real patients, according to some embodiments of the present invention.
Figure 7B:
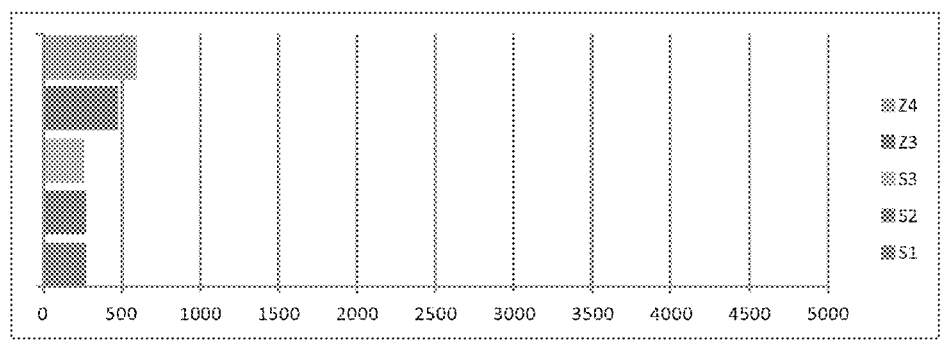
Figure 7C:
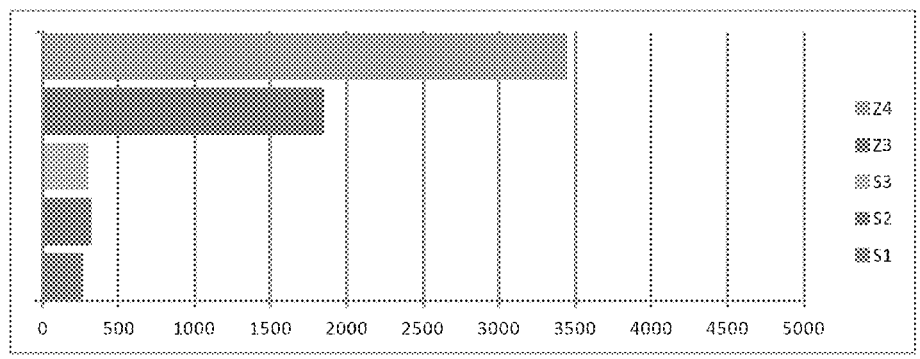
Figure 7D:
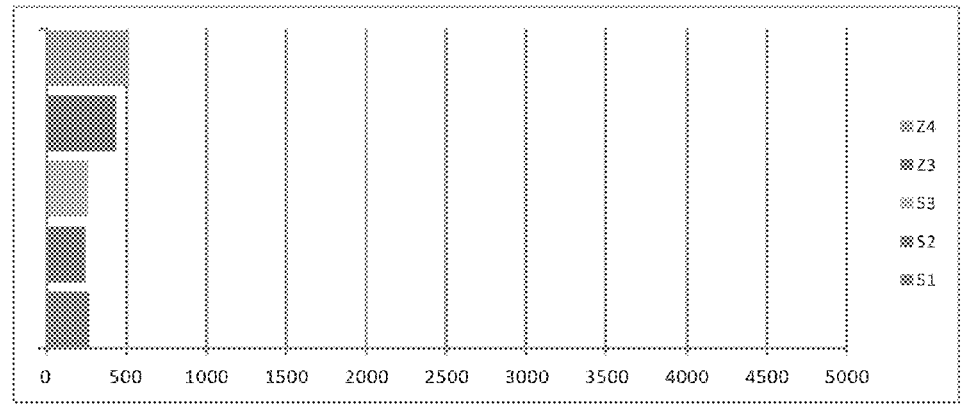
Figure 8:
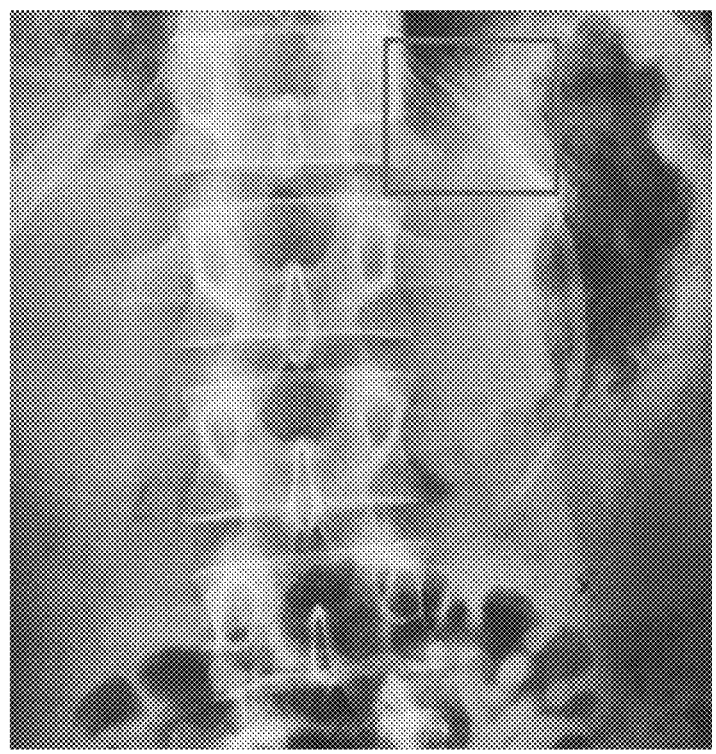
FIG. 8 is an X-ray image imaging the location of the naso/orogastric feeding tube of the naso/orogastric feeding device used for measuring impedance measures depicted in FIGS. 7C-7D.

Reference is now made to FIGS. 7A-7D which depicts real combined measures taken using a naso/orogastric feeding tube 99 having impedance sensors in segments 152, 153, for example electrodes forming impedance sensors S1-S3 which are located in LES segment 152 and electrodes forming impedance sensors Z3-Z4 which are located in esophagus segment 151. The measures are in ohm. As indicated in FIG. 7A the impedance measured in the LES is lower that the impedance measured above the LES as the LES walls are in contact with the electrodes S1-S3. FIG. 7A depicts exemplary combined impedance measure when the LES segment 152 is in the LES and the esophagus segment 151 is in the esophagus. The location of the naso/orogastric feeding tube 99 was verified by X-ray imaging. FIG. 7B depicts a change in the combined impedance measure when the LES segment 152 and the esophagus segment have were pushed into the stomach during a feeding procedure. The change reflects how the impedance reading decreases at the esophagus segment and how the impedance difference between the segments is reduced. The location of the naso/orogastric feeding tube 99 was also verified by X-ray imaging. FIG. 7A depicts another exemplary combined impedance measure measured when the naso/orogastric feeding tube 99 was positioned in an esophagus of another patient such that the LES segment 152 was in the LES and the esophagus segment 151 was in the esophagus. As shown at FIG. 8 the location of the naso/orogastric feeding tube 99 was verified by X-ray imaging. For instance, the square delimitates the location of the impedance sensors of the LES segment 151 in the LES.

According to some embodiments of the present invention, the impedance sensors are replaced with pressure sensors, such as piezoelectric pressure transducers, Force sensors, stress sensors, Piezoelectric film (PVDF) sensors, Electromagnetic sensors and/or any other sensors that can be mounted or embedded on the naso/orogastric feeding tube 99. In such embodiments impedance readings are replaced with pressure, stress, and/or force readings and the combined impedance measure is replaced with a respective combined measure.

The methods as described above are used in the fabrication of integrated circuit chips.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant methods and systems will be developed and the scope of the term control unit, a feeding tube, and feeding content is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof. The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for positioning of a naso/orogastric feeding tube, comprising
    an interface adapted to receive a plurality impedance readings from a plurality of impedance sensors disposed in a plurality of segments along a lateral surface of a naso/orogastric feeding tube; wherein one of said plurality of segments is located between 1 centimeter and 5 centimeters above another of said plurality of segments when said naso/orogastric feeding tube is in a feeding position;
    a code store for storing a code;
    a processor coupled to said interface and said code store for implementing said code, the code comprising:
        code to calculate an estimation of a position of said naso/orogastric feeding tube according to a presence or an absence of an impedance difference between different readings of said plurality impedance readings, and
        code to generate instructions for a caregiver to relocate said naso/orogastric feeding tube according to said estimation;
        code to generate instructions for initiating feeding via said naso/orogastric feeding tube when said naso/orogastric feeding tube is in said feeding position;
        wherein said impedance difference indicates whether at least one of said plurality of segments is located in the lower esophageal sphincter (LES) of a patient while another of said plurality of segments is located in the stomach of the patient.

2. The system of claim 1, wherein one of said plurality of segments is located to be in the LES when said naso/orogastric feeding tube is in a feeding position in the esophagus and another of said plurality of segments is at least 1 centimeter above the LES when said naso/orogastric feeding tube is in said feeding position.

3. The system of claim 1, further comprising a man machine interface (MMI) which is electronically connected to said processor;
    wherein said code further comprises:
        a code to monitor a combined impedance measure comprising said plurality impedance readings;
        a code to detect an intervention event according to a change in said combined impedance measure;
        a code to forward instructions to present repositioning instructions to a caregiver in response to said intervention event detection.

4. The system of claim 1, wherein said code further comprises a code to detect undesired migration of said naso/orogastric feeding tube; wherein said instructions are instructions to present an alert for indicating to said caregiver to relocate said naso/orogastric feeding tube.

5. The system of claim 1, wherein said code further comprises a code to detect a reflux while said naso/orogastric feeding tube is in said feeding position; wherein said instructions are instructions to present an alert for indicating to said caregiver about said reflux.

6. The system of claim 1, wherein said code further comprises an additional code to detect when said naso/orogastric feeding tube is in said feeding position according to a combined impedance measure comprising said plurality impedance readings.

7. The system of claim 6, wherein said additional code further comprises a code that in response to said detection perform at least one of instructing the presentation of a user interface allowing said caregiver to initiate a feeding process using said naso/orogastric feeding tube and automatically instructing a feeding machine to initiate said feeding process.

8. The system of claim 1, further comprising a fluid source which is connected to inflate at least esophageal elastic body mounted on said naso/orogastric feeding tube;
    wherein said code further comprises:
        a code to monitor a combined impedance measure comprising said plurality impedance readings;
        a code to detect an intervention event according to a change in said combined impedance measure;
        a code to forward inflating or deflating instructions to said fluid source in response to said intervention event detection.

9. The system of claim 1, further comprising a display which is electronically connected to said processor;
    wherein said code further comprises:

a code to monitor a combined impedance measure comprising said plurality impedance readings;

a code to detect an intervention event according to a change in said combined impedance measure;

a code to forward instructions to present an alert in response to said intervention event detection.

10. The system of claim 1, wherein said code further comprises:

a code to detect a misplacement of at least part of said naso/orogastric feeding tube in the trachea according to a combined impedance measure comprising said plurality impedance readings; and a code to forward instructions to present an alert in response to said misplacement detection.

11. The system of claim 1, wherein said code further comprises:

a code to monitor a combined impedance measure comprising said plurality impedance readings;

a code to detect an intervention event according to a change in said combined impedance measure;

a code to forward instructions to regulate a feeding rate in response to said intervention event detection.

12. The system of claim 1, wherein each one of said plurality of impedance sensors is a pair of electrodes.

13. The system of claim 12, wherein each of said pair of electrodes is a portion of a wire exposed by at least one recess in a lateral surface of said naso/orogastric feeding tube.

14. The system of claim 1, wherein at least one of said plurality of segments comprises at least three electrodes which are circumferentially arranged in respective said segment around a perimeter of said naso/orogastric feeding tube; wherein each one of said plurality of impedance sensors in said respective segment comprises a pair of electrodes from at least three electrodes.

15. The system of claim 1, wherein said code to generate instructions for a caregiver to relocate said naso/orogastric feeding tube according to said estimation comprises:

code to generate instructions for a caregiver to push said naso/orogastric feeding tube in response to said estimation, wherein said processor also executes the following:

code to calculate an additional estimation indicative that said plurality of segments are in the stomach based on said plurality impedance readings, and code to generate instructions for said caregiver to pull said naso/orogastric feeding tube into said feeding position in response to said additional estimation.

16. The system of claim 1, wherein said impedance difference is of more than 2000 ohm difference.

* * * * *